United States Patent [19]

McCarthy

[11] Patent Number: 5,473,104
[45] Date of Patent: Dec. 5, 1995

[54] PROCESS FOR THE PREPARATION OF L-CARNITINE

[75] Inventor: James R. McCarthy, Solana Beach, Calif.

[73] Assignee: Neurocrine Biosciences, Inc., San Diego, Calif.

[21] Appl. No.: 306,502

[22] Filed: Sep. 13, 1994

[51] Int. Cl.$^6$ .................................................. C07C 229/12
[52] U.S. Cl. .................................................................. 562/567
[58] Field of Search .................................................. 562/567

[56] References Cited

U.S. PATENT DOCUMENTS

| | | | |
|---|---|---|---|
| 3,135,788 | 6/1964 | Noguchi et al. | 260/531 |
| 3,151,149 | 9/1964 | Strack et al. | 260/465.5 |
| 3,830,931 | 8/1974 | DeFelice | 424/319 |
| 3,968,241 | 7/1976 | DeFelice | 424/319 |
| 4,070,394 | 1/1978 | Wiegand | 260/465.5 R |
| 4,075,352 | 2/1978 | DeFelice | 424/319 |
| 4,898,977 | 2/1990 | Herold et al. | 564/191 |
| 5,292,939 | 3/1994 | Hollingsworth | 562/515 |

OTHER PUBLICATIONS

CA112:179887a (1989).
CA118:191741e (1992).
Masaji Tomita and Yuzo Sendju, "Synthesis of L–carnitine," *Z. Physiol. Chem.* 169:263 (1927).
Voeffray et al., "193. L–Carnitine. Novel Synthesis and Determination of the Optical Purity," *Helv. Chim. Acta* 70:2058 (1978).
Strack et al., "Synthesis of DL–carnitine," *Ber.* 86:525 (1953).
Carter and Bhattacharyya, "Improvements in the Synthesis of DL–Carnitine," *J. Am. Chem. Soc.* 75:2503 (1953).
Strack and Lorenz, "Synthesis of DL,–D–, and L–carnitine from epichlorohydrin," *Z. Physiol. Chem* 318:129 (1960).
Jon Bremer, "Carnitine and its role in fatty acid metabolism," *TIBS* 2:207 (1977).
Jung et al., "Synthesis of L–Carnitine by Microorganisms and Isolated Enzymes," *Adv. Biochem. Eng.* 50:21 (1993).

*Primary Examiner*—José G. Dees
*Assistant Examiner*—Barbara S. Frazier
*Attorney, Agent, or Firm*—Seed and Berry

[57] ABSTRACT

There is disclosed a process for preparation of L-carnitine from (S)-3-hydroxybutyrolactone. The process is a two-step preparation in which (S)-3-hydroxybutyrolactone is first converted to a hydroxy-activated form and subsequently transformed to L-carnitine by treatment of the hydroxy-activated (S)-3-hydroxybutyrolactone with trimethylamine in water.

19 Claims, No Drawings

PROCESS FOR THE PREPARATION OF L-CARNITINE

TECHNICAL FIELD

This invention relates generally to the preparation L-carnitine from (S)-3-hydroxybutyrolactone.

BACKGROUND OF THE INVENTION

L-carnitine plays a significant role in β-oxidation of fatty acids and, as a result, has created an increasing demand for this compound in medicine (see, e.g., Bremer, *Trends Biochem. Sci.* 2:207–9, 1977). Such demand has led to the development of numerous procedures lbr production of L-carnitine, including its isolation from natural sources, synthetic chemical procedures (such as resolution of racemic mixtures of DL-carnitine), and transformation by enzymes and microorganisms.

A number of chemical methods for the synthesis of DL-carnitine are known. For example, U.S. Pat. No. 3,135,788 is directed to the preparation of DL-carnitine hydrochloride in which epichlorohydrin is first treated with trimethylamine to provide 1-chloro-2-hydroxy-4-(trimethylammonio)butane. Subsequent displacement of chloride by treatment with potassium cyanide produces the corresponding cyano compound which, upon acidic hydrolysis, yields DL-carnitine. A similar strategy was employed in U.S. Pat. No. 4.070,394 where the chloride of epichlorohydrin was initially displaced by trimethylamine and the product thus obtained treated with various metal cyanides to yield 1-cyano-2-hydroxy-4-(trimethylammonio)butane, which is then converted to DL-carnitine by hydrolysis.

The discovery of adverse effects of D-carnitine, and the questionable therapeutic effectiveness of the racemic mixture of DL-carnitine, has driven the search for a practical and economically efficient preparation of L-carnitine. To this end, optically pure L-carnitine has now been prepared by resolution from its racemic mixture. For example, U.S. Pat. No. 3,151,149 is directed to such a resolution by recrystallization using D-(+)-camphor-10-sulfonic acid. The synthesis of L-carnitine from optically pure precursors resolved from their respective racemic mixtures has also been reported. For example, racemic mixtures of 1-chloro-2-hydroxy-4-(trimethylammonio)butane have been resolved using L-(+)-tartaric acid, and the resulting enantiomerically pure chlorobutane chemically transformed to L-carnitine (Voeffray et. al., *Helv. Chim. Acta* 70:2058–64, 1987).

Optically pure L-carnitine has also been prepared from chiral compounds including (R)-4-chloro-3-hydroxybutyrate. For example, a chemomicrobiological synthesis of L-carnitine has been reported (Zhou et al., *J. Amer. Chem. Soc.* 105:5925–26, 1983) wherein optically pure (R)-4-chloro-3-hydroxybutyrate was prepared from ethylacetoacetate by reduction by baker's yeast, and then converted to L-carnitine by standard methods. Another enzymatic synthesis of (R)-4-chloro-3-hydroxybutyrate employing a coupled enzyme system of glucose dehydrogenase and alcohol dehydrogenase has also been reported (Wong et al., *J. Amer. Chem. Soc.* 107: 4028–31, 1985).

Despite the availability of L-carnitine, existing methods for its production are indirect, laborious, and economically prohibitive. Accordingly, there is a need in the art for a direct and efficient route to optically pure L-carnitine. The present invention fulfills this need, and provides further related advantages.

SUMMARY OF THE INVENTION

In brief, a two-step preparation of L-carnitine from commercially available (S)-3-hydroxybutyrolactone is disclosed. The process comprises reacting a hydroxy-activated (S)-3-hydroxybutyrolactone with an aqueous solution of trimethylamine. In the practice of this invention, L-carnitine is readily produced in enantiomeric excess from the optically pure starting material (i.e., (S)-3-hydroxybutyrolactone) at levels of at least 90%, and more typically in enantiomeric excess of at least 95%.

More specifically, in one embodiment of this invention, L-carnitine is produced from a hydroxy-activated (S)-3-hydroxybutyrolactone by treatment with a saturated solution of trimethylamine in water. In another embodiment, a co-solvent is optionally present in the aqueous trimethylamine solution. Such co-solvents include ethanol, methanol, tetrahydrofuran and acetonitrile, and may be present in the aqueous trimethylamine solution in amounts ranging from about 5% to about 50% by volume of the total solution.

Generally, the hydroxy-activated (S)-3-hydroxybutyrolactones of this invention include (S)-3-hydroxybutyrolactone alkyl and aryl sulfonates. More specifically, the hydroxy-activated (S)-3-hydroxybutyrolactones include alkyl and haloalkyl sulfonates as well as aryl, haloaryl, alkylaryl, alkoxyaryl, and nitroaryl sulfonates: alkyl sulfonates include methane, ethane, propane, isopropane, and butane sulfonates; haloalkyl sulfonates include halogenated derivatives of the above-mentioned alkyl sulfonates, and specifically include trichloromethane sulfonate, trifluoromethane sulfonate, chloroethane sulfonate, chloropropane sulfonate, and perfluorobutane sulfonate; aryl sulfonates include benzene and napthalene sulfonates, as well as various derivatives, including alkylaryl sulfonates such as alkylbenzene sulfonates (e.g., toluene, mesitylene, and triisopropylbenzene sulfonates), alkoxyaryl sulfonates including alkoxybenzene sulfonates such as methoxybenzene sulfonates, halobenzene sulfonates such as bromo-, chloro-, and fluorobenzene sulfonates, and nitroaryl sulfonates such as nitrobenzene sulfonates.

Other aspects of the invention will become evident upon reference to the following detailed description.

DETAILED DESCRIPTION OF THE INVENTION

The present invention is generally directed to a process for the preparation of carnitine, 3-hydroxy-4-(trimethylammonio)butanoate, and, more specifically, to the preparation of the optically pure L-carnitine, (R)-3-hydroxy-4-(trimethylammonio)butanoate.

Carnitine is a chiral molecule by virtue of the fact that it possesses an asymmetric carbon atom. C-3, which bears as substituents a hydrogen, a hydroxy group, a trimethylamino methyl group, and a carboxymethyl group. As such, the configuration of substituents about C-3 results in to possible absolute configurations, and therefore, two optical isomers (i.e., enantiomers) of carnitine exist. One optical isomer causes leverorotation of a plane of polarized light and is designated as the L-isomer, while the other optical isomer causes dextrorotation and is designated as the D-isomer.

As mentioned above, the present process produces L-carnitine in enantiomeric excess corresponding to the optical purity, of the starting material, (S)-3-hydroxybutyrolactone. Using such an optically pure starting material, L-carnitine in enantiomeric excess of 90%, and more typically in enantiomeric excess of 95% may readily be achieved. As used herein, the term "enantiomeric excess" refers to the optical purity of the chiral product (i.e., the percentage of one optical isomer in relation to the total amount of all of the optical isomers of the product produced). Accordingly, when the production of L-carnitine achieves an enantiomeric excess of 95% this means that 97.5% of the carnitine thus produced is the L-optical isomer.

The optical purity of L-carnitine achieved by this invention results from the stereoselective nature of the reaction of the present invention coupled with the use of an optically pure starting material. In other words, the process of the present invention is stereoselective (i.e., substantially produces a single optical isomer). Subjecting an appropriately reactive optically pure starting material (i.e., a single optical isomer of the starting material) to the process of the present invention provides an optically pure product. Thus, in the practice of the present invention, treatment of hydroxy-activated (S)-3-hydroxybutyrolactone produces L-carnitine, treatment of hydroxy-activated (R)- 3-hydroxybutyrolactone produces D-carnitine, and treatment of racemic hydroxy-activated 3-hydroxybutyrolactone produces racemic DL-carnitine.

As used herein, the term "hydroxy-activated" refers to a chemical moiety derived from a hydroxy group such that the derivative of the hydroxy group is reactive toward displacement (i.e., the derivative of the hydroxy group is a good leaving group). In the practice of the present invention, the hydroxy group of (S)-3-hydroxybutyrolactone has been activated toward displacement and subsequent L-carnitine formation by appropriate derivatization.

A representative process for the preparation of L-carnitine is presented schematically in below.

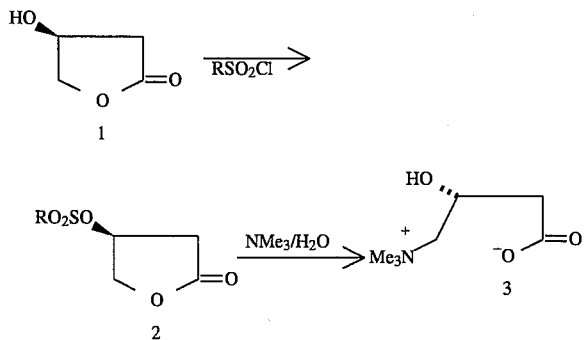

The above reaction involves a two-step process: first, an optically pure hydroxy-activated (S)-3-hydroxybutyrolactone (2) is produced from an optically active starting material, (S)-3-hydroxybutyrolactone (1); second, the hydroxy-activated (S)-3-hydroxybutyrolactone (2) is converted to L-carnitine (3) by reacting with trimethylamine in water.

The optical purity of hydroxy-activated (S)-3-hydroxybutyrolactone (2) is due to the optical purity of (S)-3-hydroxybutyrolactone (1), which is commercially available (Kaneka America Corp., New York, N.Y.) in optically pure form. The conversion of (1) to (2) is an esterification reaction and does not involve bond breakage or formation at C-3. Consequently, conversion of (1) to (2) occurs without racemization at C-3 and without loss of optical purity.

By a stereoselective reaction, the hydroxy-activated (S)-3-hydroxybutyrolactone (2) is then converted to L-carnitine (3). The transformation from (2) to (3) occurs upon treatment of (2) with an aqueous solution of trimethylamine. In the particular reaction illustrated above, the hydroxy-activated (S)-3-hydroxybutyrolactone (2) is (S)-3-hydroxybutyrolactone sulfonate, and thus the activated hydroxy group is the $—SO_3R$ moiety where R represents an alkyl or aryl group (or substituted derivatives thereof). In this embodiment, the hydroxy group of (S)-3-hydroxybutyrolactone (1) is activated toward displacement by treatment with a sulfonyl chloride to yield a sulfonic acid ester (i.e., a sulfonate). The activated hydroxy group, $—SO_3R$, is a good leaving group and thus facilitates the process of the present invention.

Without being limited to the following theory, for the formation of L-carnitine from the hydroxy-activated (S)-3-hydroxybutyrolactone, the mechanism of reaction is believed to involve the following steps. Nucleophilic attack by hydroxide ion (a species present in an aqueous solution of trimethylamine) on the lactone carbonyl of (2) is believed to occur, resulting in lactone ring opening and the generation of an alkoxide ion. The alkoxide ion then acts as a nucleophile and displaces the leaving group on its neighboring carbon atom, C-3. Such an intramolecular displacement results in an inversion of configuration of C-3. The transient product formed by the stereoselective displacement reaction is believed to be an epoxide which is immediately susceptible to nucleophilic attack by trimethylamine at C-4. The nucleophilic attack by trimethylamine results in epoxide ring opening to yield the optically pure product, L-carnitine (3), which possesses a trimethylammonium group at C-4 and a hydroxy substituted, asymmetric carbon at C-3.

In a preferred embodiment of the present invention, L-carnitine is produced from a hydroxy-activated (S)-3-hydroxybutyrolactone by treatment with an aqueous solution of trimethylamine which preferably contains a saturated amount of trimethylamine which may generally range from about 20% to about 25% by weight trimethylamine in water. In a preferred embodiment, the aqueous solution of trimethylamine is a saturated solution containing from about 23–25% by weight trimethylamine in water.

In another embodiment, a co-solvent is optionally present in the aqueous trimethylamine solution. The co-solvent serves to enhance the solubility of -the hydroxy-activated (S)-3-hydroxybutyrolactone in the predominantly aqueous reaction mixture, and thus promote L-carnitine formation. Suitable co-solvents include (but are not limited to) ethanol, methanol, tetrahydrofuran, and acetonitrile, and may be present in the aqueous trimethylamine solution in amounts ranging from about 5% to about 50% by volume of the total solution. In a preferred embodiment, the co-solvent is ethanol and is present in the aqueous trimethylamine solution in about 20% by volume of the total solution. Alternatively, the co-solvent may be added directly to the hydroxy-activated (S)-3-hydroxybutyrolactone immediately prior to the addition of the aqueous trimethylamine solution.

As mentioned above, in one embodiment of this invention the hydroxy-activated (S)-3-hydroxybutyrolactones are generally (S)-3-hydroxybutyrolactone alkyl and aryl sulfonates. Such hydroxy-activated (S)-3-hydroxybutyrolactone alkyl and aryl sulfonates include substituted alkyl and aryl sulfonates. Suitable substituted alkyl and aryl sulfonates include haloalkyl sulfonates, haloaryl, alkylaryl, alkoxyaryl, and nitroaryl sulfonates. Alkyl sulfonates include $C_{1-4}$ alkyl (e.g., methane, ethane, propane, isopropane and butane) sulfonates; and haloalkyl sulfonates include halogenated derivatives of the above-mentioned alkyl sulfonates, such as trichloromethane sulfonate, trifluoromethane sulfonate, chloroethane sulfonate, chloropropane sulfonate, and perfluorobutane sulfonate. Similarly, aryl sulfonates include benzene and napthalene sulfonates, as well as various derivatives thereof including alkylaryl sulfonates such as alkylbenzene sulfonates (e.g., toluene, mesitylene, and triisopropylbenzene sulfonates), alkoxyaryl sulfonates (e.g., alkoxybenzene sulfonates such as methoxybenzene sulfonates), haloaryl sulfonates (e.g., benzene sulfonates such as bromo-, chloro-, and fluorobenzene sulfonates), and nitroaryl sulfonates (e.g., nitrobenzene sulfonates). The aryl sulfonate derivatives of this invention may be substituted at one or more of the benzene or naphthalene ring positions. In a preferred embodiment, the hydroxy-activated (S)-3-hydroxybutyrolactone is (S)-3-hydroxybutyrolactone methane sulfonate. (The preparation of (S)-3-hydroxybutyrolactone methane sulfonate from (S)-3-hydroxybutyrolactone and its conversion to L-carnitine is described in the Example.)

The following example is provided for purposes of illustration, not limitation.

EXAMPLE

The Preparation of L-Carnitine

This example presents a representative synthesis of L-carnitine. The synthesis is a two-step process: (1) formation of a hydroxy-activated (S)-3-hydroxybutyrolactone (i.e., a methane sulfonate); and (2) conversion of the hydroxy-activated (S)-3-hydroxybutyrolactone to L-carnitine by reaction with trimethylamine in water. All solvents and reagents used in this example are commercially available (e.g., Aldrich Chemical Co., Milwaukee, Wis.) and are used as received without further purification unless otherwise stated. Optically pure (S)-3-hydroxybutyrolactone is commercially available from Kaneka America Corp. (New York, N.Y.) and is used without further purification.

A. Synthesis of a Hydroxy-Activated (S)-3-Hydroxybutyrolactone: (S)-3-Hydroxybutyrolactone Methane Sulfonate To a solution of (S) 3-hydroxybutyrolactone (1) (102 g, 1 mol) in toluene (1 L) and triethylamine (172 mL, 1.25 mol) is added a catalytic amount of 4-N,N-dimethylaminopyridine (5 g). The resulting solution is cooled to 5° C. in an ice bath and methanesulfonyl chloride (148 g, 1.3 mol) is slowly added dropwise via an addition funnel. The reaction mixture is then allowed to warm to ambient temperature with stirring. After stirring at room temperature for 16 hours, the reaction mixture is poured into ice cold brine (500 mL). After separation of the aqueous and organic layers, the organic layer is washed with ice cold 1N hydrochloric acid (2×250 mL) and brine (250 mL). The organic solution is dried over anhydrous magnesium sulfate and evaporated to dryness in vacuo. The resulting oil, (S)-3-hydroxybutyrolactone methane sulfonate ((2) where R=CH$_3$), is used directly in the next step.

B. Synthesis of L-Carnitine

To an aqueous solution of trimethylamine (250 mL), 25% by weight solution of trimethylamine in water, is added (S)-3-hydroxybutyrolactone methane sulfonate (98 g, 0.5 mol) prepared as described above. The resulting solution is stirred at room temperature 1 hr, and then heated at 100° C. in a sealed vessel for 16 hrs. Upon cooling the solution to room temperature, the reaction mixture is evaporated to dryness in vacuo using ethanol and toluene (5:1) to remove residual water by azeotropic distillation. The crude L-carnitine is triturated with anhydrous acetone (100 ml) and the purified L-carnitine thus produced is collected by filtration. $[\alpha]_D^{22}$ −31° (c 10.0, H$_2$O).

From the foregoing, it will be appreciated that, although specific embodiments of this invention have been described herein for the purposes of illustration, various modifications may be made without departing from the spirit and scope of invention. Accordingly, the invention is not limited except by the appended claims.

I claim:

1. A process for preparing L-carnitine comprising reacting a hydroxy-activated (S)-3-hydroxybutyrolactone with an aqueous solution of trimethylamine.

2. The process of claim 1 wherein L-carnitine is produced in enantiomeric excess of at least 90%.

3. The process of claim 1 wherein L-carnitine is produced in enantiomeric excess of at least 95%.

4. The process of claim 1 wherein the aqueous solution of trimethylamine contains from 20–25% by weight trimethylamine.

5. The process of claim 1 wherein the aqueous solution of trimethylamine is a saturated solution of trimethylamine in water.

6. The process of claim 1 wherein the aqueous solution contains a co-solvent.

7. The process of claim 6 wherein the co-solvent is selected from the group consisting of ethanol, methanol, tetrahydrofuran and acetonitrile.

8. The process of claim 6 wherein the co-solvent is present in the aqueous solution in an amount form 5 to 50% by volume.

9. The process of claim 1 wherein the hydroxy-activated (S)-3-hydroxybutyrolactone is an (S)-3-hydroxybutyrolactone alkyl sulfonate.

10. The process of claim 9 wherein the (S)-3-hydroxybutyrolactone alkyl sulfonate is selected from the group consisting of methane sulfonate, ethane sulfonate, propane sulfonate, isopropane sulfonate and butane sulfonate.

11. The process of claim 9 wherein the (S)-3-hydroxybutyrolactone alkyl sulfonate is methane sulfonate.

12. The process of claim 1 wherein the hydroxy-activated (S)-3-hydroxybutyrolactone is an (S)-3-hydroxybutyrolactone haloalkyl sulfonate.

13. The process of claim 12 wherein the haloalkyl sulfonate is selected from the group consisting of trichloromethane sulfonate, trifluoromethane sulfonate, chloroethane sulfonate, chloropropane sulfonate and perfluorobutane sulfonate.

14. The process of claim 1 wherein the hydroxy-activated (S)-3-hydroxybutyrolactone is an (S)-3-hydroxybutyrolactone aryl sulfonate.

15. The process of claim 14 wherein the aryl sulfonate is selected from the group consisting of benzene sulfonate, alkylbenzene sulfonate, alkoxybenzene sulfonate, halobenzene sulfonate, nitrobenzene sulfonate and napthalene sulfonate.

16. The process of claim 15 wherein the alkylbenzene sulfonate is selected from the group consisting of toluene sulfonate, mesitylene sulfonate and triisopropylbenzene sulfonate.

17. The process of claim 16 wherein the hydroxy-activated (S)-3-hydroxybutyrolactone is toluene sulfonate.

18. The process of claim 15 wherein the alkoxybenzene sulfonate is methoxybenzene sulfonate.

19. The process of claim 15 wherein the halobenzene sulfonate is selected from the group consisting of bromobenzene sulfonate, chlorobenzene sulfonate and fluorobenzene sulfonate.

* * * * *